United States Patent [19]
Kauffman et al.

[11] Patent Number: 5,364,368
[45] Date of Patent: Nov. 15, 1994

[54] STABILIZATION DEVICE FOR INTRAVASCULAR CATHETERS

[76] Inventors: Kathryn M. Kauffman; Edward L. Yancy, both of 271 West Short St., Suite 500, Lexington, Ky. 40507

[21] Appl. No.: 85,777

[22] Filed: Jul. 1, 1993

[51] Int. Cl.$^5$ ............................................. A61M 25/02
[52] U.S. Cl. .............................. 604/180; 128/DIG. 6
[58] Field of Search ................. 604/180, 174, 179; 128/DIG. 26, DIG. 6

[56] References Cited

U.S. PATENT DOCUMENTS

| | | | |
|---|---|---|---|
| 3,918,446 | 11/1975 | Buttaravoli | 604/180 |
| 3,926,185 | 12/1975 | Krzewinski | 128/DIG. 26 |
| 3,973,565 | 8/1976 | Steer | 604/180 |
| 4,059,105 | 11/1977 | Cutruzzula | 604/180 |
| 4,074,397 | 2/1978 | Rosin | 128/DIG. 26 |
| 4,484,914 | 11/1984 | Brown | 128/DIG. 26 |
| 4,534,762 | 8/1985 | Heyer | 128/DIG. 26 |
| 4,726,716 | 2/1988 | McGuire | 128/DIG. 26 |
| 4,941,882 | 7/1990 | Ward et al. | 604/180 |
| 5,207,652 | 5/1993 | Kay | 604/180 |

*Primary Examiner*—Paul J. Hirsch

[57] ABSTRACT

A stabilization device for intravascular catheters comprises a sheet of fiber reinforced material defined by first and second spaced sheet members. The first and second sheet members each have a predetermined size and shape and the same or different thickness dimension. A pair of fiber reinforced side bolsters bridge the first and second sheet members and provide a connection therebetween. The side bolsters have a thickness dimension that is greater than the thickness dimension of both the first and second sheet members to provide lateral support for an intravascular catheter. The sheet members and the side bolsters cooperate to define a framing window to facilitate unobstructed observation of the percutaneous insertion site of the intravascular catheter.

4 Claims, 1 Drawing Sheet

STABILIZATION DEVICE FOR INTRAVASCULAR CATHETERS

BACKGROUND—FIELD OF INVENTION

This invention relates to medical products, specifically stabilization of intravascular catheters.

BACKGROUND—DISCUSSION OF PRIOR ART

Most of the time, intravascular catheters are inserted into flexible body areas (e.g. wrist, neck, groin and elbow). These catheters are usually covered with unsterile tape and on top of the tape is placed a sterile clear plastic bandage. The purpose of the sterile clear plastic bandage is to prevent contamination of the catheter site. However, when the unsterile tape is placed between the catheter and sterile plastic bandage, the catheter entry site is already contaminated, thus defeating the purpose of the sterile plastic bandage.

Furthermore, neither the unsterile tape nor the sterile clear plastic bandage acts to stabilize the catheter. Consequently, due to the necessary body placement and absence of stabilizing materials, the catheters often become dislodged or bent.

If the catheter becomes dislodged or bent it can cause irritation of the surrounding tissues, infiltration of intravascular infusions into the surrounding body tissues, bleeding from the entry site and false readings from catheter transducers. The very least concern is that medical personnel will be unable to properly treat and diagnose the patients condition because of false readings from catheter transducers. Of more serious concern is the possibility that intravascular infusions infiltrate the body tissue resulting in amputation of the patient's extremity in which the catheter was inserted. The most severe consequence is the patient can bleed to death if an arterial catheter is totally dislodged from the entry site.

Another problem with existing products is their inability to remain adhered to the patients skin when they become moist due to sweat, blood, bodily fluids, water or contact with infusion fluids.

Dislodged catheters must be removed. Loose tape and bandages must be replaced. The more often a catheter is removed and a new one placed in another area of the body, the higher the risk of infection and complications. Also, the more often a catheter site is exposed when the tape and bandage are replaced, the higher the risk of infection. Not to mention, the increased cost to the patient, his insurance carrier or the public when catheters, tape and bandages are disposed and replaced with new ones.

Materials do exist which will adhere to human skin under moist conditions. However, these materials, called wound closure strips, are not presently designed to secure and stabilize catheter entry sites.

Existing products fail to maintain sterility, fail to stabilize the catheter and result in higher medical costs, higher risk of complications for the patient and consumes more materials and time than the proposed invention.

OBJECTS AND ADVANTAGES

The objects and advantages of our invention are:

(a) To provide stabilization of intravascular catheter entry sites.
(b) To permit visualization of the catheter entry site, while providing stabilization, so medical personnel may observe the entry site for infection or signs of infiltration.
(c) To increase the amount of time any single catheter can stay in a patient's body before having to be replaced or relocated to another body area.
(d) To decrease the risk of infection, infiltration, amputation of body extremities and death due to catheter dislodging and potential complications.
(e) To increase to reliability of transducer readings emitted from a catheter transducer so medical personnel may more accurately treat and diagnose the patient's condition.
(f) To decrease the cost of medical treatment for patients, their insurance carriers and the public taxpayers by increasing the longevity of catheters and the materials used to secure the catheters.
(g) To decrease the cost of medical treatment by reducing the frequency of infection, infiltration and other complications caused by catheter dislodging.
(h) To enhance medical personnel time management through reducing the frequency of catheter replacement and treatments associated with complications from catheter dislodging.

Further advantages include better adhesion of the stabilizing device under moist conditions caused by sweat, blood, bodily fluids, water and infusion fluids. The invention is made of non-allergenic material which will reduce irritation to the patient's skin and is a sterile product alleviating the need to use unsterile tape.

DRAWINGS—FIGURES

REFERENCE NUMERALS IN DRAWINGS

1 Stabilizing side bolsters
2 Catheter window
3 Fiber reinforced material
4 Pressure sensitive adhesive
5 Protective backing material

DESCRIPTION

Figure 1A:
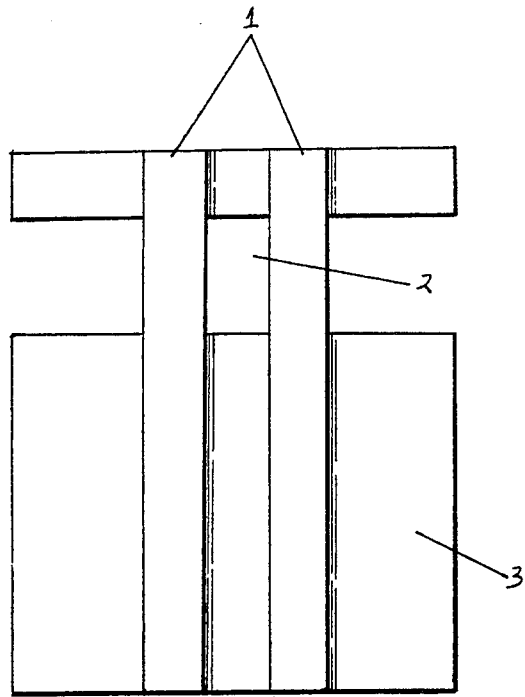
FIG. 1A is an overall single dimensional top view showing the unique shape of the invention, the relative size and length of the parallel side bolsters and the catheter window.
Figure 1B:
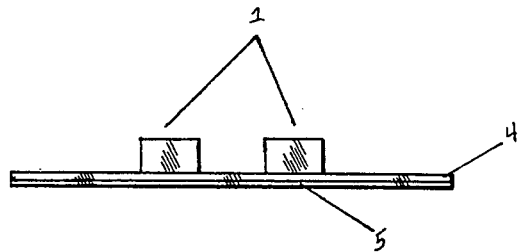
Fig 1B is a single dimensional horizontal end view showing sheet of fiber reinforced material which is coated with the pressure-sensitive adhesive, the protective backing and the side bolsters which act as the stabilizing mechanism of the structure.
Figure 1C:
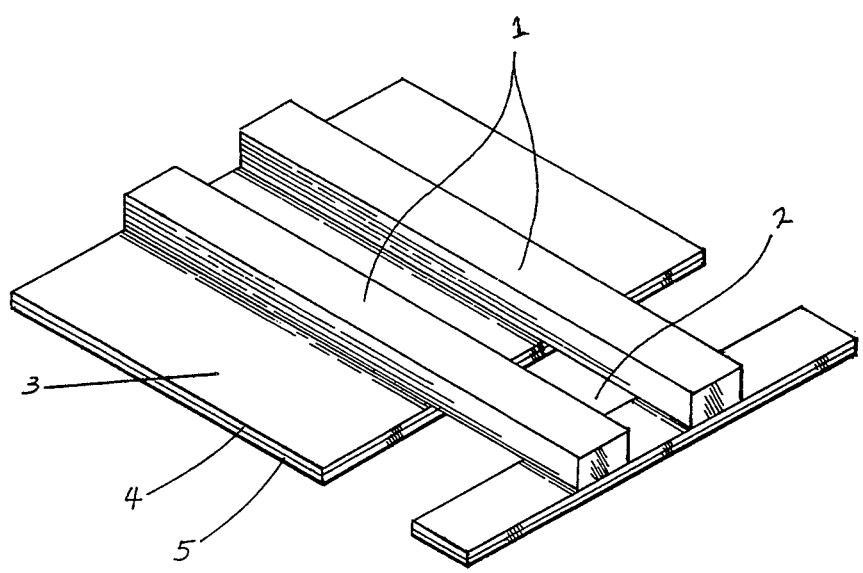
FIG. 1C is a perspective view showing the components of the invention and emphasizing the relative dimensions between the sheet of fiber reinforced material and the side bolsters.

A fiber reinforced material, 3 of FIG. 1A, with a protective backing material, 5 of FIG. 1B, is cut to a predetermined size and shape as shown in 3 of FIG. 1A. The fiber reinforced material is evenly coated on one side, as shown in 4 of FIG. 1B, with a pressure sensitive adhesive. A protective backing material covers the pressure-sensitive adhesive prior to utilization of the invention.

FIG. 1B (horizontal view) shows the additional layered thickness of the fiber reinforced material which constitutes the stabilizing side bolsters shown as 1 of FIG. 1A and FIG. 1B.

A catheter window of predetermined size and rectangular shape, 2 of FIG. 1A, is formed during the cutting process of the fiber reinforced material and protective backing, 3 of FIG. 1A and 5 of FIG. 1B respectively. The stabilizing side bolsters, 1 of FIG. 1A and FIG. 1B, are attached to the fiber reinforced material.

OPERATION

The manner of using the stabilization device for intravascular catheters is to remove the protective backing, 5 of FIG. 1B, thus exposing the bottom side of the fiber reinforced material covered with the pressure sensitive adhesive, 4 of FIG. 1B.

The stabilization device, FIG. 1A, is positioned over the intravascular catheter so that the catheter head is lodged in the catheter window, 2 of FIG. 1A, and between the stabilizing side bolsters, 1 of FIG. 1A and FIG. 1B.

We claim:

1. A stabilization device for intravascular catheters, comprising:
   a sheet of fiber reinforced material defined by a first sheet member in spaced relation with a second sheet member, said first and second sheet members each having a predetermined size and shape; and
   at least two fiber reinforced side bolsters bridging said first and second sheet members and having a thickness dimension greater than the thickness dimension of both of said sheet members,
   said side bolsters cooperating to provide lateral support for an intravascular catheter disposed therebetween and further cooperating with said first and second sheet members to define a framing window for unobstructed observation of an insertion site of said catheter.

2. The stabilization device as in claim 1, wherein said side bolsters are disposed in substantially parallel relation.

3. The stabilization device as in claim 2, wherein said framing window is substantially rectangular in shape.

4. The stabilization device as in claim 1, wherein said fiber reinforced material is evenly coated on a bottom side with a pressure-sensitive adhesive and covered by a protective backing material of the same predetermined size and shape.

* * * * *